(12) United States Patent
Senoo et al.

(10) Patent No.: US 12,083,509 B2
(45) Date of Patent: Sep. 10, 2024

(54) BETA-TYPE ZEOLITE AND CATALYST CONTAINING SAME

(71) Applicant: Mitsui Mining & Smelting Co., Ltd., Tokyo (JP)

(72) Inventors: Yuichi Senoo, Saitama (JP); Katsuhiko Hayashi, Saitama (JP); Junki Tomita, Saitama (JP); Takahiro Kogawa, Saitama (JP); Akihiro Kanno, Saitama (JP)

(73) Assignee: Mitsui Mining &Smelting Co., Ltd., Tokyo (JP)

( * ) Notice: Subject to any disclaimer, the term of this patent is extended or adjusted under 35 U.S.C. 154(b) by 296 days.

(21) Appl. No.: 17/606,912

(22) PCT Filed: Jun. 29, 2020

(86) PCT No.: PCT/JP2020/025518
§ 371 (c)(1),
(2) Date: Oct. 27, 2021

(87) PCT Pub. No.: WO2021/002322
PCT Pub. Date: Jan. 7, 2021

(65) Prior Publication Data
US 2022/0203344 A1 Jun. 30, 2022

(30) Foreign Application Priority Data
Jul. 3, 2019 (JP) ................................. 2019-124816

(51) Int. Cl.
*B01J 29/00* (2006.01)
*B01J 29/70* (2006.01)
(Continued)

(52) U.S. Cl.
CPC .......... *B01J 29/7057* (2013.01); *B01J 35/50* (2024.01); *B01J 35/58* (2024.01); *C01B 39/46* (2013.01);
(Continued)

(58) Field of Classification Search
CPC ... B01J 37/28; B01J 37/30; B01J 35/50; B01J 35/58; B01J 35/615; B01J 35/617;
(Continued)

(56) References Cited

U.S. PATENT DOCUMENTS 4,753,910 A 6/1988 Han et al.
5,200,168 A 4/1993 Apelian et al.
(Continued)

FOREIGN PATENT DOCUMENTS

CN 102249258 A 11/2011
CN 103787357 A 5/2014
(Continued)

OTHER PUBLICATIONS

Corma et al., "Isobutane/2-butene alkylation on zeolite beta: Influence of post-synthesis treatments", Applied Catalysis A: General, Elsevier, 1996, vol. 142, pp. 139-150.
(Continued)

*Primary Examiner* — Stefanie J Cohen
(74) *Attorney, Agent, or Firm* — RANKIN, HILL & CLARK LLP

(57) ABSTRACT

Provided is a beta zeolite satisfying P>76.79Q−29.514 in a range in which Q is less than 0.4011 nm, wherein, P represents an AB value that is an intensity ratio of A to B, A represents a diffraction intensity of a main peak of the beta zeolite observed by X-ray diffraction measurement, B represents a diffraction intensity of the (116) plane of α-alumina obtained by X-ray diffraction measurement under the same conditions as those for the X-ray diffraction measurement on
(Continued)

the beta zeolite, the α-alumina being the standard substance 674a distributed by the American National Institute of Standards and Technology, and Q represents a lattice interplanar spacing of the main peak of the beta zeolite observed by X-ray diffraction measurement. It is preferable that the formula (1) above is satisfied in a range in which Q is from 0.3940 to 0.4000 nm.

11 Claims, 1 Drawing Sheet

(51) Int. Cl.
    *B01J 35/50* (2024.01)
    *B01J 35/58* (2024.01)
    *C01B 39/46* (2006.01)
    *C07C 4/06* (2006.01)
(52) U.S. Cl.
    CPC ............ *C07C 4/06* (2013.01); *B01J 2229/18* (2013.01); *C01P 2002/72* (2013.01); *C07C 2529/70* (2013.01)
(58) Field of Classification Search
    CPC ............... B01J 29/7007; B01J 29/7057; B01J 29/7815; B01J 29/89; B01J 29/048; B01J 2229/32; B01J 2229/37; B01J 2229/36; B01J 2229/16; B01J 2229/18; B01J 2229/186; B01J 2229/183; C01B 39/46; C01B 39/16; C01B 39/026; C07C 4/06; C07C 2529/70; C01P 2002/72
    USPC ............................. 502/60, 64; 423/713, 718
    See application file for complete search history.

(56) References Cited

U.S. PATENT DOCUMENTS

| | | | |
|---|---|---|---|
| 2012/0190534 A1 | 7/2012 | Itabashi et al. | |
| 2015/0147268 A1* | 5/2015 | Yoon ..................... | C01B 39/48 423/700 |
| 2016/0263563 A1* | 9/2016 | Liu ........................ | C01B 39/026 |
| 2019/0262815 A1 | 8/2019 | Nishikawa et al. | |

FOREIGN PATENT DOCUMENTS

| | | |
|---|---|---|
| CN | 104667995 A | 6/2015 |
| EP | 3056272 B1 | 3/2021 |
| JP | 63-270307 A | 11/1988 |
| JP | 2010-215434 A | 9/2010 |
| JP | 6339306 B1 | 6/2018 |

OTHER PUBLICATIONS

International Search Report (ISR) dated Aug. 25, 2020 filed in PCT/JP2020/025518.

Kao et al., "27 Al and 19 F Solid-State NMR Studies of Zeolite H-β Dealuminated with Ammonium Hexafluorosilicate", Journal of Physical Chemistry Part B, 2003, vol. 107, No. 15, pp. 3367-3375; Cited in European Office Action (EPOA) dated Apr. 2, 2024.

Marques et al., "n-Heptane cracking on dealuminated HBEA zeolites", Catalysis Today, Elsevier, 2005, vol. 107-108, pp. 726-733.

Berreghis et al., "Acetylation of 2-methoxynaphthalene with acetic anhydride over a series of dealuminated HBEA zeolites", Catalysis letters 68, 2000, pp. 121-127, Retrieved from the Internet: URL: <https://link.springer.com/content/pdf/10.1023/A:1019083420175.pdf>, retrieved on Jul. 8, 2022.

Wang et al., "Dealumination of organic structure-directing agent (OSDA) free beta zeolite for enhancing its catalytic performance in n-hexane cracking", Microporous and Mesoporous Materials, Elsevier, 2016, vol. 220, pp. 275-281.

A.M. Camiloti et al., "Acidity of Beta zeolite determined by TPD of ammonia and ethylbenzene disproportionation", Applied Catalysis A: General, Jun. 1999, vol. 182, No. 1, pp. 107-113; Cited in Japanese Office Action dated Jun. 4, 2024.

Yasunobu Miyamoto et al., "Acidity of β zeolite with different Si/Al2 ratio as measured by temperature programmed desorption of ammonia", Microporous and Mesoporous Materials, Nov. 2000, vol. 40, No. 1-3, pp. 271-281; Cited in Japanese Office Action dated Jun. 4, 2024.

Mahesh S. Edake et al., "Solvent free selective isomerization of p-diethylbenzene to m-diethylbenzene using modified Hβ zeolites", Advanced Materials Letters, Oct. 1, 2024 Vol. 5 No. 10, pp. 550-556; Cited in Japanese Office Action dated Jun. 4, 2024.

* cited by examiner

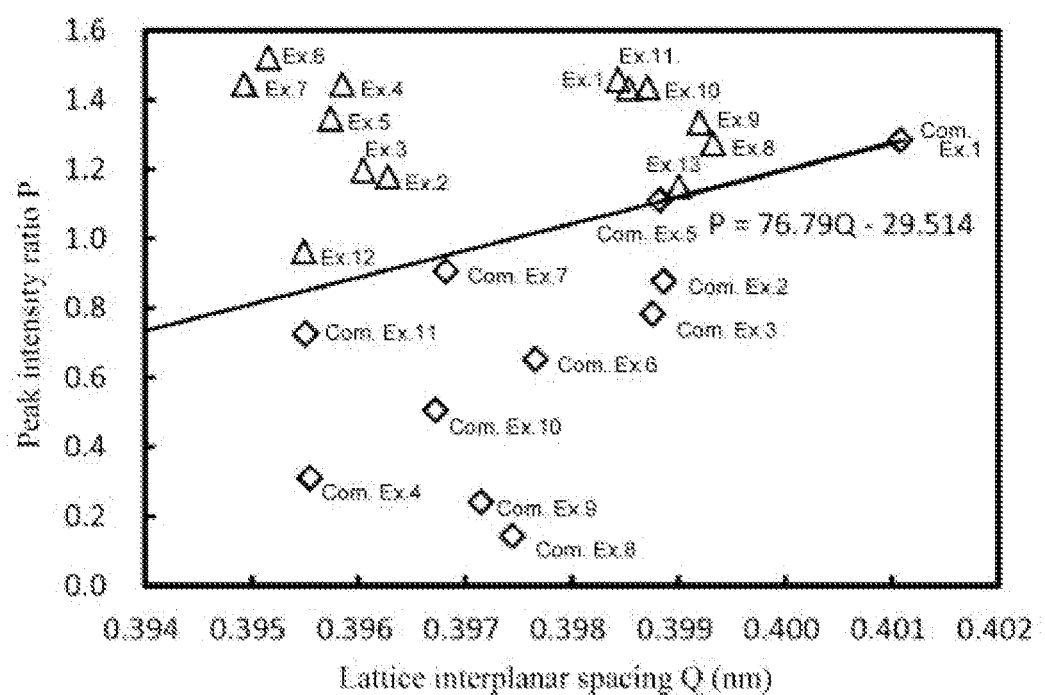

BETA-TYPE ZEOLITE AND CATALYST CONTAINING SAME

TECHNICAL FIELD

The present invention relates to a beta zeolite. Also, the present invention relates to a catalyst containing the beta zeolite.

BACKGROUND ART

Synthetic zeolites are crystalline aluminosilicates and each have sub-nano-sized uniform pores resulting from the crystal structure thereof. Taking advantage of this feature, synthetic zeolites are industrially used as molecular sieve adsorbents that adsorb only molecules with specific sizes, adsorption separators that adsorb molecules with strong affinities, or catalyst bases. Beta zeolites, which are a type of such zeolites, are currently used in large quantities all over the world as catalysts in the petrochemical industry and as adsorbents for treating automobile exhaust gas. Conventionally, beta zeolites have been synthesized using an organic structure directing agent (hereinafter, also referred to as an "OSDA"), but in recent years, a method for synthesizing a beta zeolite without using an OSDA has been proposed (see Patent Literature 1).

Beta zeolites synthesized without using an OSDA (hereinafter, also referred to as "OSDA-free beta zeolites") have a low Si/Al ratio and exhibit high crystallinity. Due to this feature, OSDA-free beta zeolites are characterized by having high ion exchange capacity derived from a low Si/Al ratio and high durability and high selectivity derived from high crystallinity. However, generally, in order to use zeolite in a wide range of application, it is important to adjust the Si/Al ratio according to the purpose of use, in consideration of the affinity with a reactant (differences in hydrophilicity/hydrophobicity and polarity). That is to say, in order to utilize high crystallinity of an OSDA-free beta zeolite in a wide range of application, a technique is necessary that dealuminates the zeolite while maintaining the crystallinity.

Known conventional techniques for dealumination of a beta zeolite are disclosed in Patent Literatures 2 and 3, for example. In Patent Literature 2, dealumination is performed by bringing a beta zeolite into contact with a dicarboxylic acid solution containing oxalic acid. In Patent Literature 3, dealumination is performed by sequentially performing water vapor treatment and mineral acid treatment in this order on a beta zeolite.

CITATION LIST

Patent Literature

Patent Literature 1: US 2012190534A1
Patent Literature 2: U.S. Pat. No. 5,200,168A
Patent Literature 3: JP 2010-215434A

SUMMARY OF INVENTION

Technical Problem

However, as a result of the study conducted by the inventors of the present invention, it was found that the use of the techniques disclosed in Patent Literatures 2 and 3 to dealuminate a beta zeolite results in a reduction in crystallinity of the beta zeolite. Due to this, the dealuminated beta zeolite has poor durability. Furthermore, since high Si/Al ratio and high crystallinity cannot be achieved at the same time, high crystallinity can be utilized only in a limited Si/Al ratio range, which is disadvantageous in terms of applicability. Therefore, it is an object of the present invention to provide a beta zeolite that has high crystallinity in a wide Si/Al ratio range.

Solution to Problem

The present invention provides a beta zeolite satisfying formula (1) below in a range in which Q is less than 0.4011 nm, $$P > 76.79Q - 29.514 \quad (1).$$

wherein, P represents an AB value that is an intensity ratio of A to B,

A represents a diffraction intensity of a main peak of the beta zeolite observed by X-ray diffraction measurement, B represents a diffraction intensity of the (116) plane of α-alumina obtained by X-ray diffraction measurement under the same conditions as those for the X-ray diffraction measurement on the beta zeolite, the α-alumina being the standard substance 674a distributed by the American National Institute of Standards and Technology, and Q represents a lattice interplanar spacing of the main peak of the beta zeolite observed by X-ray diffraction measurement.

Also, the present invention provides a beta zeolite having D1 (mmol/g)/Z (mmol/g) of 0.40 or greater, D1 (mmol/g)/Z (mmol/g) being a ratio of D1 to Z, wherein, D1 (mmol/g) represents an amount of adsorbate compound desorbed per gram of the beta zeolite at 300° C. or greater and less than 500° C., the amount of adsorbate compound being measured by temperature programmed desorption method using ammonia as the adsorbate compound, and Z (mmol/g) represents an amount of aluminum per gram of the beta zeolite.

Also, the present invention provides a catalyst containing the beta zeolite.

Advantageous Effects of Invention

According to the present invention, a beta zeolite that has high crystallinity in a wide Si/Al ratio range is provided.

BRIEF DESCRIPTION OF DRAWINGS

FIG. 1 is a graph on which the relationship between peak intensity ratio P and lattice interplanar spacing Q is plotted for beta zeolites obtained in examples and comparative examples.

DESCRIPTION OF EMBODIMENTS

Hereinafter, the present invention will be described based on a preferred embodiment thereof. The inventors of the present invention have conducted in-depth study on beta zeolites having high crystallinity in a wide Si/Al ratio range and found that a beta zeolite having such characteristics satisfies a specific relationship between the intensity of a peak obtained by X-ray diffraction measurement and the lattice interplanar spacing obtained by X-ray diffraction measurement, and the present invention was thus accomplished. The peak intensity obtained by X-ray diffraction measurement is mainly related to the crystallinity of the beta zeolite. On the other hand, the lattice interplanar spacing obtained by X-ray diffraction measurement is mainly related to the Si/Al ratio. Note that, as used in the present invention, the term "a wide Si/Al ratio range" means a region of an Si/Al ratio range in which the Si/Al ratio is more than 5. Moreover, as used in the present invention, the "Si/Al ratio" refers to the mole ratio of Si to Al.

In the present invention, when the diffraction intensity of a main peak of a beta zeolite observed by X-ray diffraction measurement is taken as A, the diffraction intensity of the (116) plane of α-alumina, which is the standard substance 674a distributed by the American National Institute of Standards and Technology, the intensity being observed by X-ray diffraction measurement under the same conditions as those for the X-ray diffraction measurement on the beta zeolite, is taken as B, an AB value, which is the intensity ratio of A to B, is taken as P, and the lattice interplanar spacing, or in other words, the d value of the (302) plane observed by X-ray diffraction measurement is taken as Q, the beta zeolite is regarded as having high crystallinity in a wide Si/Al ratio range if there is a specific relationship between P and Q. Note that the (302) plane of a beta zeolite is a lattice plane corresponding to the main diffraction peak.

The value of P is obtained by X-ray diffraction measurement performed on a sample obtained by mixing the beta zeolite that is to be measured and α-alumina, which is a standard substance, in the same volume. Specifically, the beta zeolite that has been sufficiently dried in dry air at 200° C. beforehand and α-alumina, which is a standard substance, are separately filled in respective glass cells with a constant volume under the same force and then taken out, the whole amounts of beta zeolite and α-alumina are mixed in a mortar, and the mixture is subjected to the measurement. The mass ratio of the beta zeolite to the standard substance in that case is about 1.0:2.4.

The intensity A of the main peak of the beta zeolite obtained by this X-ray diffraction measurement and the diffraction intensity B of the (116) plane of α-alumina, which is a standard substance, obtained by this X-ray diffraction measurement are determined, and P is calculated from the values of A and B. Intensities A and B are the heights of peaks obtained by X-ray diffraction measurement. Moreover, the main peak of a beta zeolite is generally observed in the range of 2θ=22.10° to 23.58°. The diffraction peak of the (116) plane of α-alumina, which is a standard substance, is generally observed in a range of 2θ=57.40° to 57.60°. The reason why the diffraction peak of the (116) plane is adopted as the diffraction peak of the α-alumina is that the diffraction peak of the beta zeolite is not observed in the vicinity the diffraction peak of the (116) plane and the diffraction peak of the (116) plane has high intensity, and thus the accuracy of measurement can be improved.

For example, RINT-TTR III manufactured by Rigaku Corporation is used for X-ray diffraction measurement. Cu Kα (0.15406 nm, 50 kV, 300 mA) is used as the X-ray source. The measurement range is 2θ=5 to 80°, the scan speed is 20°/sec, and the scan step is 0.02°. PDXL2 software manufactured by Rigaku Corporation is used for analysis. After removing the background, the Kα1 position is set as the peak position and fitting is performed using a split-type pseudo Voigt function to obtain the diffraction intensity and the d value. The Scherrer equation is used when analyzing the full width at half maximum. The Scherrer constant is set to 0.9400.

In the present invention, it is preferable that the above-described P and Q satisfy formula (1) below in the range in which Q is less than 0.4011 nm. In particular, beta zeolites that satisfy the formula (1) below in the range in which Q is from 0.3940 nm to 0.4000 nm, and particularly from 0.3940 nm to 0.3970 nm, have even higher crystallinity in a wide Si/Al ratio range. Furthermore, due to the high crystallinity, such beta zeolites exhibit excellent hydrothermal durability. In this case, the value of P is preferably 0.75 or greater, and for higher crystallinity, the value of P is more preferably 1.14 or greater, and even more preferably 1.35 or greater.

$$P > 76.79Q - 29.514 \quad (1)$$

In the beta zeolite of the present invention, it is also preferable that the formula (1) above is satisfied in the range in which Q is 0.3963 nm or less, and the full width at half maximum of the main peak of the beta zeolite observed by X-ray diffraction measurement is 0.135° or less. With Q and the full width at half maximum satisfying this relationship, the beta zeolite can exhibit high crystallinity while having a wide Si/Al ratio range. In this case, for the purpose of maintaining a small full width at half maximum, Q is more preferably 0.3960 nm or less, and even more preferably 0.3958 nm or less. Moreover, for the purpose of preventing an extreme reduction in acid sites due to dealumination, Q is preferably 0.3949 nm or greater. With Q satisfying this range, the beta zeolite can have a wide Si/Al ratio range.

The full width at half maximum is more preferably 0.125° or less, and even more preferably 0.122° or less. The full width at half maximum serves as a measure of the level of crystallinity of beta zeolites, and the smaller the full width at half maximum, the higher the crystallinity. The beta zeolite of the present invention in which the full width at half maximum is less than or equal to the above-described value exhibits high crystallinity. Furthermore, due to the high crystallinity, the beta zeolite of the present invention exhibits excellent hydrothermal durability.

The Si/Al ratio of the beta zeolite of the present invention can take a wide range of values. The Si/Al ratio of the beta zeolite of the present invention is greater than 5 and 600 or less, particularly from 6 to 600, and more particularly from 10 to 550. The Si/Al ratio can be determined through quantitative analysis of Si and Al using ICP emission spectroscopy using an aqueous solution in which the beta zeolite is dissolved as a sample.

The beta zeolite of the present invention may be directly synthesized using an OSDA, or may be synthesized using a seed crystal and without using an OSDA, in other words, may be an OSDA-free beta zeolite. A method for directly synthesizing a beta zeolite using an OSDA is known in the art. A method for producing an OSDA-free beta zeolite is disclosed in Patent Literature 1 above, for example. Usually, when an attempt is made to increase the Si/Al ratio of an OSDA-free beta zeolite by dealumination, there is a problem in that the crystallinity of the OSDA-free beta zeolite is likely to be reduced. On the other hand, in the beta zeolite of the present invention, this problem is suppressed, and therefore, it is advantageous that the beta zeolite of the present invention is an OSDA-free beta zeolite for the reason that high durability is derived from high crystallinity, high selectivity in catalytic reactions is derived from high crystallinity, and excellent selectivity for a wide Si/Al ratio range is achieved.

With respect to the beta zeolite of the present invention, when an amount of adsorbate compound desorbed at 300° C. or greater and less than 500° C. is taken as D1, and the amount of adsorbate compound desorbed at 500° C. or greater and less than 700° C. is taken as D2 wherein the amount of adsorbate compound is measured by temperature programmed desorption method using ammonia as the adsorbate compound, the value (mmol/g) of D2−D1 is preferably −0.25 mmol/g or greater, more preferably −0.12 mmol/g or greater, and even more preferably 0.03 mmol/g or greater. A beta zeolite exhibiting such characteristics has a relatively high Si/Al ratio. Furthermore, a beta zeolite exhibiting such characteristics exhibits excellent retention rates of specific surface area and internal specific surface area before and after a hydrothermal durability test.

Furthermore, the above-described D2−D1 value (mmol/g) of the beta zeolite of the present invention is preferably −1.31 mmol/g or greater and less than −0.25 mmol/g, more preferably −0.70 mmol/g or greater and less than −0.25 mmol/g, and even more preferably −0.30 mmol/g or greater and less than −0.25 mmol/g. A beta zeolite exhibiting such characteristics can have a relatively low Si/Al ratio, a large number of acid sites, and a large number of adsorption sites that are involved in catalytic reactions.

Furthermore, with respect to the beta zeolite of the present invention, when the amount of aluminum per gram of beta zeolite is taken as Z (mmol/g), the value of D1 (mmol/g)/Z (mmol/g), which is the ratio of the above-described D1 to Z, is preferably 0.40 or greater, more preferably 0.5 or greater, and even more preferably 0.7 or greater. The D1/Z value serves as a measure of the amount of acid sites per mole of aluminum contained in the beta zeolite. A beta zeolite having a D1/Z value greater than or equal to this value has high crystallinity in a wide Si/Al ratio range and also exhibits excellent hydrothermal durability. From this viewpoint, the D1/Z value is preferably 2.3 or less, and more preferably 1.0 or less.

A beta zeolite with D1/Z being greater than or equal to the above-described value is suitably produced using a method that will be described later. With the method that will be described later, dealumination progresses while the crystal structure of the beta zeolite is maintained, and therefore aluminum that is present outside the crystal is easily removed, while on the other hand, aluminum that is present inside the crystal is unlikely to be removed. As a result, a large amount of aluminum that contributes to acid sites remains in the dealuminated beta zeolite, and therefore, the beta zeolite of the present invention has a large amount of acid sites per mole of aluminum. In contrast to this, the crystal structure of a conventional beta zeolite is likely to collapse, and therefore, during dealumination, in addition to aluminum that does not contribute to acid sites, even aluminum that is present inside the crystal and contributes to acid sites is removed, and due to this removal of aluminum, the amount of acid sites per mole of aluminum decreases.

The amount of adsorbate compound that is desorbed in the temperature programmed desorption (TPD) can be measured using the following method, for example.

As pretreatment, the temperature of about 0.05 g of sample is raised to 500° C. in a He gas, kept at 500° C. for an hour, and then cooled to 100° C. Next, at a sample temperature of 100°, an ammonia gas diluted with a helium gas (concentration of ammonia in helium: 5 vol %; hereinafter also referred to as "5% $NH_3$—He") is added to cause ammonia to be adsorbed. Thereafter, in order to remove physically adsorbed ammonia, purging in a helium gas is performed for 30 minutes. After that, the temperature is raised from 100° C. to 700° C. under the conditions at a helium gas flow rate of 30 mL/min and a temperature increase rate of 10° C./min, and the desorption amount is measured.

BELCAT-II and BEL MASS both manufactured by MicrotracBEL Corp. are used as measurement apparatuses. Then, the areas of the above-described D1 and D2 segments in a TCD signal obtained by the measurement are calculated using Chem Master waveform separation software available from MicrotracBEL Corp. The areas are calculated without using fitting with a normal distribution or the like, and integrated values of the signal within the respective segments are used. With the use of a calibration curve prepared using the relationship between flow rate and area when flowing a 5% $NH_3$—He balance gas at a predetermined flow rate, the area values of the TCD signal are converted into the amounts of ammonia desorbed. Furthermore, the converted values were divided by the mass of the sample after the end of the present measurement to thereby calculate the values of D1 and D2 (mmol/g).

The BET specific surface area of the beta zeolite of the present invention is preferably from 200 $m^2/g$ to 800 $m^2/g$, more preferably from 400 $m^2/g$ to 650 $m^2/g$, and even more preferably from 450 $m^2/g$ to 650 $m^2/g$. A beta zeolite having a BET specific surface area in this range is useful as an adsorbent for various compounds and a catalyst for various reactions.

In relation to the BET specific surface area, the internal specific surface area of the beta zeolite of the present invention is preferably from 200 $m^2/g$ to 800 $m^2/g$, more preferably from 390 $m^2/g$ to 550 $m^2/g$, and even more preferably from 420 $m^2/g$ to 550 $m^2/g$. A beta zeolite having an internal specific surface area in this range is even more useful as an adsorbent for various compounds and a catalyst for various reactions. The internal specific surface area means the micropore specific surface area.

The methods for measuring the BET specific surface area and the internal specific surface area are as described below.

As a measurement apparatus, 3-Flex manufactured by Micromeritics is used. Heating treatment (400° C., 4 hours) is performed in a vacuum at 0.1 Pa, and then, an adsorption isotherm is measured (gas used: 99.999 vol % nitrogen) at the liquid nitrogen temperature (−196° C.) under the conditions of an air constant temperature oven temperature of 45° C. and an equilibrium adsorption time of 300 s.

The BET specific surface area is obtained in the following manner. With the use of Micromeritics software 3Flex Version 4.02, the BET equation is applied to a range of relative pressure $p/p_0$ (ratio of adsorption equilibrium pressure p to saturated vapor pressure $p_0$)=0.01 to 0.15 on the adsorption isotherm for nitrogen measured at −196° C.

The internal specific surface area is obtained in the following manner. With respect to the adsorption isotherm for nitrogen measured at −196° C., the thickness t of an adsorption layer is calculated from the relative pressure $p/p_0$ using the formula (2) below, and a t-plot in which the horizontal axis represents t (nm) and the vertical axis represents the adsorption amount ($cm^3/g$) is generated. A linear approximation is performed on the adsorption amount in the range of 0.36 nm≤t≤0.50 nm, and an internally stored program of Micromeritics software 3Flex Version 4.02 is applied, to thereby calculate the micropore volume and the micropore specific surface area (internal specific surface area).

$$t=[13.99/(0.034-\log(p/p_0))]^{0.5} \qquad (2)$$

The beta zeolite of the present invention may be of a proton type, an ammonium type, a sodium type, a potassium type, or a lithium type. Furthermore, the beta zeolite of the present invention may be a beta zeolite in which ion exchange sites have been replaced with transition metal ions through ion exchange. Examples of the transition metal that can be ion-exchanged include iron, copper, cobalt, nickel, chromium, molybdenum, manganese, vanadium, titanium, cerium, ruthenium, platinum, silver, and iridium. When the beta zeolite of the present invention is in a state of being ion-exchanged with a transition metal, its performance as a catalyst for various reactions may be further improved. Ion exchange with transition metal ions can be performed, for example, by dispersing the beta zeolite in an aqueous ammonium nitrate solution to obtain an ammonium-type beta zeolite, and then using the method described in JP 2014-019601A.

It is also possible that an oxide of phosphorus, zirconium, zinc, or silicon is present on the surface of the beta zeolite of the present invention. Beta zeolites having oxides of these elements on their surface have an appropriately controlled amount of acid on the surface, and can be even more useful as adsorbents for various compounds and catalysts for various reactions. In order to allow oxides of these elements to be present on the surface of beta zeolites, it is sufficient to use, for example, an impregnation method, an evaporative drying method, or a surface modification method using a coupling agent such as a silane coupling agent or a zirconium coupling agent. Whether or not oxides of these elements are present on the surface can be confirmed through XPS (X-ray photoelectron spectroscopy), for example.

It is preferable that the beta zeolite of the present invention contains at least one element M selected from titanium, tin, zinc, niobium, tantalum, and zirconium, because the element M can be an active site for various chemical reactions. In order to cause the element M to be contained in the zeolite, it is sufficient to use, for example, a known method such as an impregnation method or an evaporative drying method. In particular, it is preferable that the at least one element M is contained in the framework of zeolite, because it has an excellent carrying capacity for polyvalent metal cations and can be an active site for various chemical reactions. From these viewpoints, the value of Si/(M+Al) as expressed in an atomic ratio is preferably from 4 to 500, more preferably from 4 to 300, and even more preferably from 4 to 40. In order to cause the element M to be contained in the framework of zeolite, it is sufficient to use, for example, a known method such as a hydrothermal synthesis method, a dry gel conversion method, or a solid phase crystallization method.

The beta zeolite of the present invention can be suitably obtained by dealuminating a beta zeolite synthesized using or without using an OSDA. During the dealumination, it is desirable to minimize a reduction in the crystallinity of the beta zeolite. For this purpose, it is preferable to bring the beta zeolite into contact with an ammonium salt. More specifically, it is preferable to bring a sodium-type, a proton-type, or an ammonium-type beta zeolite into contact with an aqueous ammonium salt solution to remove aluminum from the framework of the zeolite, thereby obtaining a beta zeolite with an increased Si/Al ratio. In particular, the beta zeolite to be dealuminated is preferably an OSDA-free beta zeolite.

The above-described ammonium salt may be either an organic ammonium salt or an inorganic ammonium salt. Examples of the organic ammonium salt include an organic acid ammonium salt such as ammonium oxalate. Examples of the inorganic ammonium salt include ammonium fluoride, ammonium fluorosilicate, ammonium fluoroborate, ammonium fluorophosphate, ammonium fluorotitanate, and ammonium fluorozirconate. These ammonium salts may be used alone or in a combination of two or more.

Dealumination using an ammonium salt can be performed by adding an ammonium salt to an aqueous beta zeolite dispersion. The concentration of beta zeolite in the aqueous dispersion is preferably from 3 g/mL to 300 g/mL, more preferably from 6 g/mL to 150 g/mL, and even more preferably from 10 g/mL to 30 g/mL, from the viewpoint of smoothly performing dealumination while maintaining the crystallinity of the beta zeolite.

The form in which the ammonium salt may be added to the aqueous dispersion may be either an aqueous solution or a powder form. The concentration of ammonium salt in an aqueous solution obtained by adding an ammonium salt in powder form, or an aqueous solution thereof, to the aqueous beta zeolite dispersion is preferably from 0.01 mol/L to 3 mol/L, more preferably from 0.05 mol/L to 2 mol/L, and even more preferably from 0.1 mol/L to 1 mol/L, from the viewpoint of smoothly performing dealumination while maintaining the crystallinity of the beta zeolite.

The mixing of the aqueous beta zeolite dispersion with the aqueous ammonium salt solution may be performed with or without heating. The liquid temperature is preferably from 0° C. to 100° C., more preferably from 25° C. to 90° C., and even more preferably from 25° C. to 60° C., from the viewpoint of smoothly performing dealumination while maintaining the crystallinity of the beta zeolite.

The beta zeolite may be subjected to pretreatment, prior to dealumination of the beta zeolite. Examples of the pretreatment include calcination treatment and water vapor treatment of the beta zeolite. If the beta zeolite is subjected to such pretreatment, the dealumination can be facilitated.

The above-described pretreatment is preferably performed after the beta zeolite is made into a sodium-type, a proton-type, or an ammonium-type beta zeolite. In the case of performing calcination treatment as the pretreatment, either an oxygen-containing atmosphere or a non-oxygen-containing atmosphere may be used. It is preferable to perform calcination treatment in an oxygen-containing atmosphere such as the air, because in this case calcination can be performed easily. The calcination temperature is preferably from 400° C. to 800° C., more preferably from 500° C. to 700° C., and even more preferably from 500° C. to 600° C. Provided that the calcination temperature is within the above-described range, the calcination time is preferably from 0.5 hours to 20 hours, more preferably from 1 hour to 10 hours, and even more preferably from 1 hour to 5 hours.

In the case of performing water vapor treatment as the pretreatment, it is sufficient to allow the beta zeolite to stand in a water vapor atmosphere or to arrange the raw material beta zeolite in a water vapor flow. For example, the beta zeolite may be exposed to water vapor using an apparatus shown in FIG. 1 of JP 2013-112546A. The temperature of water vapor is preferably from 90° C. to 800° C., more preferably from 200° C. to 700° C., and even more preferably from 300° C. to 700° C. Provided that the temperature of water vapor is within the above-described range, the time of exposure to water vapor is preferably from 1 hour to 50 hours, more preferably from 2 hours to 20 hours, and even more preferably from 5 hours to 20 hours.

Regardless of whether or not pretreatment is performed before dealumination, aftertreatment may be performed after dealumination. As the aftertreatment, it is preferable to perform acid treatment. If acid treatment is performed, a beta zeolite having high crystallinity in a wide Si/Al ratio range can be obtained more easily. Examples of the acid that can be used in the acid treatment include various mineral acids such as nitric acid, hydrochloric acid, and sulfuric acid. Of these mineral acids, it is preferable to use nitric acid.

The concentration of an aqueous acid solution that can be used in the acid treatment is preferably from 0.001 N to 20 N, more preferably from 0.01 N to 13 N, and even more preferably from 0.1 N to 3 N. Note that "N" represents the normality. The amount of aqueous acid solution added is preferably from 10 mL to 500 mL, more preferably from 10 mL to 300 mL, and even more preferably from 10 mL to 30 mL, with respect to 1 g of beta zeolite after dealumination.

The mixing of the aqueous beta zeolite dispersion with the aqueous acid solution may be performed with or without heating. In the case where the mixing is performed with heating, the liquid temperature is preferably from 40° C. to 100° C., more preferably from 60° C. to 100° C., and even more preferably from 80° C. to 100° C.

The thus obtained beta zeolite of the present invention has high crystallinity in a wide Si/Al ratio range. Taking advantage of this feature, the beta zeolite of the present invention is suitably used as an adsorbent for various compounds and a catalyst for various chemical reactions. For example, a conventional beta zeolite with a low Si/Al ratio is excessively hydrophilic due to the low Si/Al ratio and tends to inhibit diffusion and adhesion of a hydrophobic reactant, and therefore has a limited use as a catalyst for hydrophobic reactants; however, the beta zeolite of the present invention has an Si/Al ratio in an appropriate range and hence suppressed hydrophilicity, and therefore can be suitably used as a catalyst for hydrophobic reactants. For example, the beta zeolite of the present invention is useful as a catalyst for cracking a long-chain hydrocarbon. Examples of the long-chain hydrocarbon include saturated or unsaturated hydrocarbons having 4 to 60 carbon atoms.

In the case where the beta zeolite of the present invention is used as a catalyst, there is no limitation on the form thereof. For example, the catalyst can be used in a film form, a pellet form, a tablet form, a ring form, an irregular-shaped form, a rod form, an irregular-shaped, grooved form, a honeycomb form, a spherical form, a granular form, a microspherical form, a flake form, an agglomerated form, or in a form of being coated on or inside a base material in a honeycomb form or the like. In that case, the catalyst may optionally contain a binder based on $Al_2O_3$, $SiO_2$, $ZrO_2$, $SnO_2$, $TiO_2$, $CeO_2$, $ZnO_2$, $Nb_2O_5$, $Ta_2O_5$, $P_2O_5$, $La_2O_3$, or $Ga_2O_3$, or a combination of these compounds.

The percentage content of the beta zeolite of the present invention in the catalyst can be set as desired, and is preferably from 1 mass % to 100 mass %, more preferably from 10 mass % to 90 mass % and even more preferably from 20 mass % to 80 mass %.

In the case where the catalyst containing the beta zeolite of the present invention is processed into any of the aforementioned forms, comparison of the X-ray diffraction intensity ratio between the beta zeolite and α-alumina, which is a standard substance, is performed in the following manner. First, the percentage content (mass %) of the beta zeolite in the catalyst is calculated. Next, an amount of α-alumina, which is a standard substance, corresponding to the calculated percentage content of the beta zeolite is mixed with the beta zeolite, and the mixture is pulverized. The pulverized product is subjected to X-ray diffraction measurement, and comparison of the X-ray diffraction intensity ratio between the beta zeolite and α-alumina, which is a standard substance, can thereby be performed.

Since an X-ray diffraction pattern of the beta zeolite is different from that of a binder component, the diffraction pattern of the binder component and the diffraction pattern of the beta zeolite can be appropriately separated from each other by using software.

On the other hand, the percentage content (mass %) of the beta zeolite in the catalyst can be calculated in the following manner, for example, although it varies depending on the type of binder.

(A) A Case in which the Binder is Other than $Al_2O_3$ and $SiO_2$

The percentage content (mass %) of the beta zeolite in the catalyst can be calculated by analyzing the $Al_2O_3$ content and the $SiO_2$ content using ICP emission spectroscopy.

(B) A Case in which the Binder is $Al_2O_3$ or $SiO_2$

The chemical bonding and the electronic state of Si and Al in the beta zeolite are generally different from the chemical bonding and the electronic state of $SiO_2$ and $Al_2O_3$ of the binder component. Therefore, through $^{29}Si$-NMR and $^{27}Al$-NMR measurement, for example, and observation of the difference in chemical shifts, Si and Al derived from the beta zeolite can be distinguished from Si and Al derived from the binder, and the quantitative ratios therebetween can be estimated based on NMR intensities. Moreover, since the Si/Al ratio in the beta zeolite can be calculated through evaluation of $^{29}Si$-NMR as described in, for example, Scientific and Technical Reports of Graduate School of Engineering and Resource Science, Akita University, No. 22, October 2001, the percentage content (mass %) of the beta zeolite can be calculated by obtaining the difference between the calculated value of the Si/Al ratio in the beta zeolite and the Si/Al ratio of the entire catalyst obtained by ICP emission spectroscopy.

EXAMPLES

Hereinafter, the present invention will be described in more detail by way of examples. However, the scope of the present invention is not limited to these examples.

Example 1

(1) Preparation of Seed Crystal

A beta zeolite with an Si/Al ratio of 9 was synthesized using tetraethylammonium hydroxide as an OSDA by stirring and heating at 165° C. for 96 hours according to a conventionally known method using sodium aluminate as an alumina source, and fine powder silica (Mizukasil P707) as a silica source. The obtained material was calcined at 550° C. for 10 hours in an air flow in an electric furnace to produce seed crystals containing no organic matter.

(2) Preparation of OSDA-Free Beta Zeolite

First, 0.235 g of sodium aluminate and 1.828 g of 36% sodium hydroxide were dissolved in 13.9 g of pure water. A mixture of 2.024 g of fine powder silica (Cab-O-sil, M-5) and 0.202 g of the above-mentioned seed crystals was gradually added to the above-mentioned aqueous solution and mixed by stirring to obtain a reaction mixture with a composition of $SiO_2/Al_2O_3=40$, $Na_2O/SiO_2=0.275$, $H_2O/SiO_2=25$. This reaction mixture was placed in a 60-mL airtight container made of stainless steel and allowed to stand and heated at 140° C. for 46 hours under autogenous pressure without aging and stirring. After cooling the airtight container, the product was filtered and washed with warm water to obtain a white powder. It was seen through X-ray diffraction measurement that the product was a sodium-type OSDA-free beta zeolite containing no impurities. As a result of ICP emission spectroscopic analysis, the Si/Al ratio was 5.0.

(3) Preparation of Ammonium-Type OSDA-Free Beta Zeolite

Then, 1 g of the sodium-type OSDA-free beta zeolite was dispersed in 30 mL of 2 mol/L aqueous ammonium nitrate solution. The dispersion was held at 80° C. for 24 hours. The dispersion was then filtered, washed with a sufficient amount of distilled water, and dried at 100° C. overnight. In this manner, an ammonium-type OSDA-free beta zeolite was obtained.

(4) Dealumination of OSDA-Free Beta Zeolite

Then, 1 g of the above-mentioned ammonium-type OSDA-free beta zeolite was dispersed in 30 mL of water to obtain a dispersion. Ammonium fluorosilicate was used as a dealuminating agent. Then, 5.35 g of ammonium fluorosilicate powder reagent was added to the OSDA-free beta zeolite dispersion (equivalent to 1 mol/L of aqueous ammonium fluorosilicate solution). The solution was held at 60° C. for 3 hours. Subsequently, filtration and washing with pure water were repeated. The obtained hydrous powder was dried at 100° C. for 12 hours or more. In this manner, an OSDA-free beta zeolite powder with an Si/Al ratio of 10 was obtained.

Example 2

Before the dealumination of the OSDA-free beta zeolite in Example 1, the zeolite was calcined as pretreatment. The calcination was performed at 500° C. for 2 hours in the air. Otherwise, the same procedures as those of Example 1 were performed.

Example 3

Before the dealumination of the OSDA-free beta zeolite in Example 1, the zeolite was exposed to water vapor as pretreatment. The exposure of the zeolite was performed at 500° C. for 20 hours in a 1.2 L/min air flow with a partial pressure of water vapor of about 7 kPa. Otherwise, the same procedures as those of Example 1 were performed.

Example 4

After the dealumination of the OSDA-free beta zeolite in Example 3, acid treatment using nitric acid was performed as aftertreatment. Nitric acid was dissolved in water to obtain a 0.1 mol/L aqueous solution. Then, 1 g of dealuminated OSDA-free beta zeolite powder was dispersed in 30 mL of the aqueous nitric acid solution with a concentration of 0.1 mol/L, and the dispersion was mixed to perform the acid treatment. The mixing temperature was 80° C., and the mixing time was 20 hours. Otherwise, the same procedures as those of Example 3 were performed.

Example 5

The concentration of the aqueous nitric acid solution used for the acid treatment in Example 4 was set to 1 mol/L. Also, the mixing temperature during the acid treatment was set to 100° C., and the mixing time was set to 8 hours. Otherwise, the same procedures as those of Example 4 were performed.

Example 6

The concentration of the aqueous nitric acid solution used for the acid treatment in Example 4 was set to 3 mol/L. Also, the mixing temperature during the acid treatment was set to 100° C., and the mixing time was set to 8 hours. Otherwise, the same procedures as those of Example 4 were performed.

Example 7

The concentration of the aqueous nitric acid solution used for the acid treatment in Example 4 was set to 3 mol/L. Also, the mixing temperature during the acid treatment was set to 100° C., and the mixing time was set to 20 hours. Otherwise, the same procedures as those of Example 4 were performed.

Example 8

The concentration of the aqueous ammonium fluorosilicate solution used for dealumination in Example 1 was set to 0.05 mol/L. Otherwise, the same procedures as those of Example 1 were performed.

Example 9

The concentration of the aqueous ammonium fluorosilicate solution used for the dealumination in Example 1 was set to 0.1 mol/L. Otherwise, the same procedures as those of Example 1 were performed.

Example 10

The concentration of the aqueous ammonium fluorosilicate solution used for the dealumination in Example 1 was set to 0.3 mol/L. Otherwise, the same procedures as those of Example 1 were performed.

Example 11

The concentration of the aqueous ammonium fluorosilicate solution used for the dealumination in Example 1 was set to 0.5 mol/L. Otherwise, the same procedures as those of Example 1 were performed.

Example 12

The OSDA-free beta zeolite in Example 3 was exposed to water vapor at 700° C. The partial pressure of water vapor was about 1.8 times that of Example 3. The exposure time was set to 20 hours. Otherwise, the same procedures as those of Example 3 were performed.

Example 13

First, 7 g of choline chloride powder was added to 7 g of ultrapure water and stirred until completely dissolved. Then, 0.12 g of tin chloride ($SnCl_2$) powder was added to the above-mentioned aqueous choline chloride solution and stirred until completely dissolved. Subsequently, 1.4 g of the OSDA-free beta zeolite powder obtained in Example 8 was added to the above-mentioned aqueous solution and stirred at room temperature for 17 hours. After that, the mixture was allowed to stand for 24 hours, and the supernatant was removed after the powder had settled. Then, 50 mL of ethanol was added to the remaining slurry and stirred at room temperature for 30 minutes, and the mixture was filtered and washed. The filtration and washing was repeated a total of three times. The obtained solid matter was dried at 60° C. for 12 hours. Then, the temperature was raised to 550° C. at a temperature increase rate of 2° C./min, followed by calcination at 550° C. for 6 hours. In this manner, an OSDA-free beta zeolite powder containing tin was obtained.

The Si/Al ratio obtained by elemental analysis was 6, and the Sn concentration was 2.0 mass %. This OSDA-free beta zeolite powder containing tin was analyzed by TEM-EDX, and Sn was detected in most regions of the powder. Moreover, it was confirmed that at least a portion of Sn was deposited on the OSDA-free beta zeolite powder.

Comparative Example 1

The dealumination in Example 1 was not performed. Otherwise, the same procedures as those of Example 1 were performed.

Comparative Example 2

The dealumination in Example 2 was not performed. Otherwise, the same procedures as those of Example 2 were performed.

Comparative Example 3

The dealumination in Example 3 was not performed. Otherwise, the same procedures as those of Example 3 were performed.

Comparative Example 4

A beta zeolite including, as a starting material for synthesis, the OSDA described in the process of "(1) Preparation of seed crystal" in Example 1 was prepared and used as Comparative Example 4. The Si/Al ratio was 9.

Comparative Example 5

The present comparative example was an example in which dealumination was performed using the method disclosed in Patent Literature 2.
As in Example 1, an OSDA-free beta zeolite was synthesized using a seed crystal. Oxalic acid was dissolved in water to obtain a 0.2 mol/L aqueous oxalic acid solution. Then, 1 g of the OSDA-free beta zeolite was mixed with the above-mentioned aqueous oxalic acid solution to thereby perform dealumination. The mixing temperature was 60° C., and the mixing time was 1 hour. In this manner, an OSDA-free beta zeolite with an Si/Al ratio of 7 was obtained.

Comparative Example 6

Before the dealumination of the OSDA-free beta zeolite with oxalic acid in Comparative Example 5, the zeolite was calcined as pretreatment. The calcination was performed at 500° C. for 2 hours in the air. Otherwise, the same procedures as those of Comparative Example 5 were performed.

Comparative Example 7

Before the dealumination of the OSDA-free beta zeolite with oxalic acid in Comparative Example 5, the zeolite was exposed to water vapor as pretreatment. The exposure of the zeolite was performed at 500° C. for 20 hours in a 1.2 L/min air flow with a partial pressure of water vapor of about 7 kPa. Otherwise, the same procedures as those of Comparative Example 5 were performed.

Comparative Example 8

The present comparative example was an example in which dealumination was performed using the method disclosed in Patent Literature 3.
As in Example 1, an OSDA-free beta zeolite was synthesized using a seed crystal. Nitric acid was dissolved in water to obtain a 0.4 mol/L aqueous nitric acid solution. Then, 1 g of the OSDA-free beta zeolite was mixed with the above-mentioned aqueous nitric acid solution to thereby perform dealumination. The mixing temperature was 60° C., and the mixing time was 1 hour.

Comparative Example 9

Before the acid treatment with nitric acid in Comparative Example 8, the zeolite was calcined as pretreatment. The calcination was performed at 500° C. for 2 hours in the air. Otherwise, the same procedures as those of Comparative Example 8 were performed.

Comparative Example 10

Before the acid treatment with nitric acid in Comparative Example 8, the zeolite was exposed to water vapor as pretreatment. The exposure of the zeolite was performed at 500° C. for 20 hours in a 1.2 L/min air flow with a partial pressure of water vapor of about 7 kPa. Otherwise, the same procedures as those of Comparative Example 8 were performed.

Comparative Example 11

A beta zeolite including an OSDA as a starting material for synthesis was prepared in the same manner as in the process of "(1) Preparation of seed crystal" in Example 1, except that the starting material composition was adjusted so that an Si/Al ratio of 19 was achieved, and the prepared beta zeolite was used as Comparative Example 11.

Evaluation 1

The beta zeolites obtained in the examples and the comparative examples were subjected to X-ray diffraction measurement using the above-described method, to obtain the values of A, B, P, Q, and the full width at half maximum of the main peak that have been described above. Furthermore, the Si/Al ratio was obtained by performing elemental analysis. Table 1 below shows the results. FIG. 1 shows the results of plotting the obtained values of P and Q on a graph.

Evaluation 2

The beta zeolites obtained in the examples and the comparative examples were subjected to nitrogen adsorption measurement using the above-described method, to obtain the BET specific surface area and the internal specific surface area. Table 2 shows the results.

Evaluation 3

The beta zeolites obtained in the examples and the comparative examples were subjected to measurement of the desorption amount through temperature programmed desorption using the above-described method. Table 2 shows the results. Table 2 also shows the results with respect to D1/Z.

Evaluation 4

The beta zeolites obtained in the examples and the comparative examples were subjected to a hydrothermal durability test, and X-ray diffraction measurement was performed after the test, to obtain the values of A, B, P, and the full width at half maximum of the main peak that have been described above. Moreover, after the hydrothermal durability test, nitrogen adsorption measurement was performed using the above-described method, to obtain the BET specific surface area and the internal specific surface area. Furthermore, the retention rates of the BET specific surface area and the internal specific surface area before and after the hydrothermal durability test were obtained. Table 3 shows the results.

The hydrothermal durability test was performed by placing 0.35 g of sample in a tubular furnace having a diameter of 5 cm. The temperature of the furnace was raised from room temperature to 800° C. in 1.5 hours, and maintained at this temperature for 16.5 hours. Meanwhile, air containing 10 vol % water vapor was caused to flow in the furnace at a flow rate of 1166 mL/min.

Evaluation 5

In order to confirm durability, the catalytic activity of the beta zeolites obtained in Example 3 and Comparative Example 11 in a hexane cracking reaction was evaluated using the following procedures.

Before the evaluation, the beta zeolites in powder form were molded and sized. Specifically, 1 to 2 g of beta zeolite powder was filled into a tablet mold with an inner diameter of 20 mm, and then, pressure molding was performed at 0.4 MPa using a hydraulic press, to obtain a pellet with a diameter of 20 mm. The obtained pellet was appropriately pulverized on a sieve and sized to 500 to 600 μm, and the resulting particles were used as a catalyst.

A catalytic reaction was conducted using a fixed-bed normal pressure flow reactor shown in FIG. 6 of Japanese Patent No. 5470592. Hexane serving as a reactant was supplied from a syringe using a syringe pump and introduced into a helium gas serving as a carrier gas. Hexane supplied from the syringe pump was introduced into a preheated vaporizing chamber, and therefore evaporated into a gas. This gas was entrained in the carrier gas. A stainless steel pipe with an inner diameter of 2 mm was used as a gas line of the reactor. The vaporized hexane was heated to an appropriate temperature using a heater from the outside of this stainless steel pipe and thereby prevented from condensing. A quartz tube with an inner diameter of 8 mm was used as a reaction tube. Then, 100 mg of the previously sized beta zeolite catalyst was filled into the quartz tube, and a catalyst layer was held in a central portion of the reaction tube using quartz wool. As reaction pretreatment, the temperature was raised to 650° C. at a temperature increase rate of about 7° C./min in an air flow, and kept in this atmosphere for 1 hour. Subsequently, the air flow was switched to a helium flow, and the helium gas in which hexane was entrained was supplied to the catalyst layer to start the catalytic reaction. The partial pressure of hexane was 5.0 kPa. After the start of the reaction, each time a predetermined period of time had elapsed, a six-way valve was switched, and the reaction product accumulated in a sampling loop was introduced into a gas chromatograph and separated in a capillary column, followed by qualitative and quantitative analysis of products and unreacted substances using a hydrogen flame detector (FID), and time dependence of the conversion of hexane and the yield of propylene was thus obtained.

The W/F during the catalytic reaction was 19.8 g-catalyst h (mol-hexane)$^{-1}$ for each case. After the end of the reaction, the reaction system was allowed to cool naturally in a helium flow. Table 4 shows the results. The selectivity for products with different number of carbon atoms was obtained in terms of carbon atoms. The yield of propylene was obtained from "conversion x selectivity for propylene". Note that the reaction temperature was measured at a location between the heater that was installed so as to heat the quartz reaction tube of the fixed-bed normal temperature flow reactor from the outside and the reaction tube.

TABLE 1

| | Zeolite | | | α-Al$_2$O$_3$ | | | | |
|---|---|---|---|---|---|---|---|---|
| | Diffraction intensity A (cps) | Full width at half maximum (°) | Lattice interplanar spacing Q (nm) | Diffraction intensity B (cps) | P (A/B) | Si/Al ratio | Amount of Si (mmol/g) | Amount of Al (mmol/g) |
| Ex. 1 | 92892 | 0.107 | 0.3984 | 63757 | 1.46 | 10 | 15.35 | 1.53 |
| Ex. 2 | 75184 | 0.135 | 0.3963 | 63776 | 1.18 | 23 | 16.07 | 0.69 |
| Ex. 3 | 76255 | 0.125 | 0.3960 | 63730 | 1.20 | 24 | 16.13 | 0.66 |
| Ex. 4 | 92078 | 0.118 | 0.3958 | 63780 | 1.44 | 78 | 15.32 | 0.20 |
| Ex. 5 | 85789 | 0.117 | 0.3957 | 63724 | 1.35 | 147 | 16.57 | 0.11 |
| Ex. 6 | 96983 | 0.113 | 0.3952 | 63700 | 1.52 | 280 | 16.62 | 0.06 |
| Ex. 7 | 92060 | 0.114 | 0.3949 | 63791 | 1.44 | 544 | 16.65 | 0.03 |
| Ex. 8 | 81209 | 0.120 | 0.3993 | 63780 | 1.27 | 6 | 14.72 | 2.27 |
| Ex. 9 | 85031 | 0.116 | 0.3992 | 63790 | 1.33 | 7 | 14.80 | 2.18 |
| Ex. 10 | 91475 | 0.113 | 0.3987 | 63750 | 1.43 | 8 | 15.08 | 1.83 |
| Ex. 11 | 91347 | 0.111 | 0.3985 | 63740 | 1.43 | 8 | 15.13 | 1.80 |
| Ex. 12 | 61385 | 0.122 | 0.3955 | 63792 | 0.96 | 33 | 15.68 | 0.47 |
| Ex. 13 | 73356 | 0.134 | 0.3990 | 63753 | 1.15 | 6 | 10.79 | 1.67 |
| Com. Ex. 1 | 81885 | 0.105 | 0.4011 | 63755 | 1.28 | 5 | 14.13 | 3.12 |
| Com. Ex. 2 | 56002 | 0.144 | 0.3989 | 63740 | 0.88 | 5 | 14.13 | 2.93 |
| Com. Ex. 3 | 50022 | 0.196 | 0.3988 | 63761 | 0.78 | 5 | 14.13 | 2.93 |
| Com. Ex. 4 | 19903 | 0.685 | 0.3955 | 63772 | 0.31 | 9 | 15.15 | 1.64 |
| Com. Ex. 5 | 70864 | 0.117 | 0.3988 | 63734 | 1.11 | 7 | 14.83 | 2.14 |
| Com. Ex. 6 | 41659 | 0.194 | 0.3977 | 63760 | 0.65 | 8 | 15.12 | 1.80 |
| Corn. Ex. 7 | 57827 | 0.136 | 0.3968 | 63771 | 0.91 | 9 | 15.18 | 1.69 |
| Corn. Ex. 8 | 9235 | 0.431 | 0.3974 | 63729 | 0.14 | 10 | 15.43 | 1.49 |
| Corn. Ex. 9 | 15423 | 0.365 | 0.3971 | 63761 | 0.24 | 13 | 15.70 | 1.18 |
| Com. Ex. 10 | 32321 | 0.255 | 0.3967 | 63753 | 0.51 | 13 | 15.67 | 1.17 |
| Com. Ex. 11 | 46216 | 0.203 | 0.3955 | 63721 | 0.73 | 19 | 15.96 | 0.83 |

TABLE 2

| | Before hydrothermal durability test | | | | |
|---|---|---|---|---|---|
| | Nitrogen adsorption measurement | | Temperature programmed desorption measurement | | |
| | BET specific surface area (m²/g) | Internal specific surface area (m²/g) | Desorption amount at 300° C. or greater and less than 500° C. D1 (mmol/g) | Desorption amount at 500° C. or greater and less than 700° C. D2 (mmol/g) | D2 − D1 | D1/Z |
| Ex. 1 | 600 | 528 | 0.73 | 0.03 | −0.70 | 0.48 |
| Ex. 2 | 504 | 444 | 0.39 | 0.09 | −0.30 | 0.56 |
| Ex. 3 | 503 | 446 | 0.30 | 0.05 | −0.25 | 0.46 |
| Ex. 4 | 443 | 399 | 0.11 | 0.14 | 0.03 | 0.54 |
| Ex. 5 | 451 | 405 | 0.07 | 0.36 | 0.30 | 0.58 |
| Ex. 6 | 480 | 429 | 0.06 | 0.49 | 0.43 | 0.99 |
| Ex. 7 | 446 | 401 | 0.07 | 0.51 | 0.44 | 2.22 |
| Ex. 8 | 594 | 529 | 1.39 | 0.16 | −1.24 | 0.61 |
| Ex. 9 | 636 | 548 | 1.40 | 0.09 | −1.31 | 0.64 |
| Ex. 10 | 591 | 522 | 1.18 | 0.05 | −1.13 | 0.65 |
| Ex. 11 | 614 | 533 | 1.20 | 0.06 | −1.13 | 0.66 |
| Ex. 12 | 446 | 392 | 0.23 | 0.11 | −0.12 | 0.48 |
| Ex. 13 | 535 | 485 | 0.66 | 0.14 | −0.53 | 0.40 |
| Com. Ex. 1 | 640 | 576 | 1.23 | 0.18 | −1.05 | 0.39 |
| Com. Ex. 2 | 629 | 561 | 0.69 | 0.22 | −0.47 | 0.24 |
| Com. Ex. 3 | 636 | 554 | 0.53 | 0.18 | −0.35 | 0.18 |
| Com. Ex. 4 | 709 | 437 | 0.31 | 0.02 | −0.29 | 0.19 |
| Com. Ex. 5 | 652 | 594 | 0.82 | 0.17 | −0.65 | 0.38 |
| Com. Ex. 6 | 700 | 626 | 0.53 | 0.27 | −0.26 | 0.29 |
| Com. Ex. 7 | 653 | 535 | 0.44 | 0.15 | −0.29 | 0.26 |
| Com. Ex. 8 | 373 | 336 | 0.32 | 0.14 | −0.19 | 0.22 |
| Com. Ex. 9 | 552 | 498 | 0.31 | 0.11 | −0.20 | 0.27 |
| Com. Ex. 10 | 624 | 559 | 0.42 | 0.20 | −0.22 | 0.36 |
| Com. Ex. 11 | 620 | 498 | 0.19 | 0.06 | −0.13 | 0.23 |

TABLE 3

| | After hydrothermal durability test | | | | | | | |
|---|---|---|---|---|---|---|---|---|
| | Zeolite | | α-Al₂O₃ | | Nitrogen adsorption measurement | | | |
| | Diffraction intensity A (cps) | Full width at half maximum (°) | Diffraction intensity B (cps) | P (A/B) | BET specific surface area (m²/g) | Internal specific surface area (m²/g) | BET specific surface area retention rate (%) | Internal specific surface area retention rate (%) |
| Ex. 1 | 60093 | 0.134 | 63775 | 0.94 | 483 | 425 | 81 | 80 |
| Ex. 2 | 71261 | 0.125 | 63768 | 1.12 | 454 | 403 | 90 | 91 |
| Ex. 3 | 77708 | 0.123 | 63734 | 1.22 | 510 | 455 | 101 | 102 |
| Ex. 4 | 78190 | 0.115 | 63762 | 1.23 | 510 | 453 | 115 | 113 |
| Ex. 5 | 85813 | 0.119 | 63758 | 1.35 | 468 | 431 | 104 | 106 |
| Ex. 6 | 79243 | 0.126 | 63720 | 1.24 | 499 | 452 | 104 | 105 |
| Ex. 7 | 81032 | 0.125 | 63737 | 1.27 | 459 | 412 | 103 | 103 |
| Ex. 8 | 61509 | 0.134 | 63749 | 0.96 | 494 | 400 | 83 | 76 |
| Ex. 9 | 75951 | 0.124 | 63795 | 1.19 | 501 | 419 | 79 | 76 |
| Ex. 10 | 67630 | 0.126 | 63751 | 1.06 | 503 | 431 | 85 | 83 |
| Ex. 11 | 76890 | 0.131 | 63732 | 1.21 | 535 | 453 | 87 | 85 |
| Ex. 12 | 61106 | 0.120 | 63787 | 0.96 | 488 | 426 | 109 | 109 |
| Ex. 13 | 69792 | 0.134 | 63741 | 1.09 | 451 | 376 | 84 | 78 |
| Com. Ex. 1 | 56004 | 0.129 | 63720 | 0.88 | 495 | 395 | 77 | 69 |
| Com. Ex. 2 | 50592 | 0.130 | 63731 | 0.79 | 485 | 413 | 77 | 74 |
| Com. Ex. 3 | 59610 | 0.126 | 63765 | 0.93 | 498 | 414 | 78 | 75 |
| Com. Ex. 4 | 12090 | 0.827 | 63778 | 0.19 | 393 | 248 | 55 | 57 |
| Com. Ex. 5 | 51747 | 0.135 | 63729 | 0.81 | 474 | 362 | 73 | 61 |
| Com. Ex. 6 | 56273 | 0.154 | 63761 | 0.88 | 476 | 361 | 68 | 58 |
| Com. Ex. 7 | 58071 | 0.135 | 63779 | 0.91 | 502 | 403 | 77 | 75 |
| Com. Ex. 8 | 4921 | 0.371 | 63740 | 0.08 | 69 | 65 | 19 | 19 |
| Com. Ex. 9 | 17756 | 0.221 | 63759 | 0.28 | 251 | 202 | 46 | 41 |
| Com. Ex. 10 | 43959 | 0.171 | 63756 | 0.69 | 424 | 324 | 68 | 58 |
| Com. Ex. 11 | 39283 | 0.230 | 63732 | 0.62 | 450 | 360 | 73 | 72 |

As shown in Tables 1 to 3, it can be seen that the beta zeolites of the examples that satisfied the relationship expressed by the formula (1) above exhibited higher retention rates of the BET specific surface area and the internal specific surface area before and after the hydrothermal durability test, compared with those of the comparative examples. This indicates that the beta zeolites of the examples have high crystallinity.

Also, it can be seen that the beta zeolites of the examples in which D1 (mmol/g)/Z (mmol/g) was 0.40 or greater exhibited higher retention rates of the BET specific surface area and the internal specific surface area before and after the hydrothermal durability test, compared with those of the comparative examples.

In the comparative examples, since the crystallinity of the beta zeolites collapsed due to dealumination, in addition to aluminum that does not contribute to acid sites, a large amount of aluminum that contributes to acid sites was removed, and accordingly, the D1/Z values were reduced.

On the other hand, the beta zeolites of the examples were dealuminated while maintaining their crystal structures, and therefore, aluminum that contributes to acid sites, which is more strongly related to the crystal structure than aluminum that does not contribute to acid sites, was unlikely to be removed, and it is conceivable that this was the reason for the relatively high D1/Z values. That is to say, it is conceivable that a beta zeolite with a D1/Z value of 0.40 or greater indicates that the beta zeolite has a wide Si/Al ratio range while maintaining high crystallinity.

TABLE 4

| | Reaction time elapsed (min) | Conversion (%) | Yield of propylene (%) |
|---|---|---|---|
| Ex. 3 | 55 | 66.7 | 24.8 |
| | 105 | 60.0 | 21.6 |
| | 155 | 51.4 | 20.6 |
| | 205 | 58.9 | 22.6 |
| | 255 | 56.1 | 20.7 |
| Com. Ex. 11 | 55 | 57.8 | 18.0 |
| | 105 | 40.9 | 12.1 |
| | 155 | 28.1 | 9.3 |
| | 205 | 22.9 | 7.0 |
| | 255 | 18.0 | 5.5 |

As shown in Table 4, it can be seen that, when hexane cracking was performed using the beta zeolite obtained in Example 3 as the catalyst, propylene, which is a useful substance as a chemical raw material, was generated in high yield, compared with that of Comparative Example 11. Moreover, it can be seen that, when the beta zeolite obtained in Example 3 was used as the catalyst, the retention rate against the reaction time elapsed, or in other words, the durability was higher than that of Comparative Example 11. It is conceivable that this result was due to the high durability of crystallinity of the beta zeolites of the examples.

The invention claimed is:

1. A beta zeolite satisfying formula (1) below in a range in which Q is less than 0.4011 nm, $$P > 76.79Q - 29.514 \quad (1),$$

wherein, P represents an A/B value that is an intensity ratio of A to B,

A represents a diffraction intensity of a main peak of the beta zeolite observed by X-ray diffraction measurement, B represents a diffraction intensity of the (116) plane of α-alumina obtained by X-ray diffraction measurement under the same conditions as those for the X-ray diffraction measurement on the beta zeolite, the α-alumina being the standard substance 674a distributed by the American National Institute of Standards and Technology, and Q represents a lattice interplanar spacing of the main peak of the beta zeolite observed by X-ray diffraction measurement.

2. The beta zeolite according to claim 1, wherein the formula (1) is satisfied in a range in which Q is from 0.3940 to 0.4000 nm.

3. The beta zeolite according to claim 1, wherein the formula (1) is satisfied in a range in which Q is 0.3963 nm or less, and a full width at half maximum of the main peak of the beta zeolite observed by X-ray diffraction measurement is 0.135° or less.

4. The beta zeolite according to claim 1, which is synthesized without using an organic structure directing agent.

5. The beta zeolite according to claim 1, which is ion-exchanged with a transition metal ion.

6. The beta zeolite according to claim 1, comprising an oxide of phosphorus, zirconium, zinc, or silicon on a surface of the beta zeolite.

7. The beta zeolite according to claim 1, comprising at least one element selected from the group consisting of titanium, tin, zinc, niobium, tantalum, and zirconium.

8. The beta zeolite according to claim 7, comprising at least one element selected from titanium, tin, zinc, niobium, tantalum, and zirconium in a framework of the beta zeolite.

9. A catalyst comprising the beta zeolite according to claim 1.

10. The catalyst according to claim 9, being a catalyst for cracking a long-chain hydrocarbon.

11. The catalyst according to claim 9, having a film form or a pellet form.

* * * * *